US005756005A

United States Patent [19]
Ghosh et al.

[11] Patent Number: 5,756,005
[45] Date of Patent: May 26, 1998

[54] STABILIZATION OF NON-HALOGENATED 3-ISOTHIAZOLONES IN AGGRESSIVE SYSTEMS

[75] Inventors: Tirthankar Ghosh, Oreland; John Robert Mattox, Perkasie, both of Pa.

[73] Assignee: Rohm and Haas Company, Philadelphia, Pa.

[21] Appl. No.: 731,228

[22] Filed: Oct. 11, 1996

Related U.S. Application Data

[60] Provisional application No. 60/007,166, Nov. 1, 1995.

[51] Int. Cl.$^6$ ............................................. C09K 15/16
[52] U.S. Cl. ............................................. 252/405
[58] Field of Search .......................... 252/405; 548/213

[56] References Cited

U.S. PATENT DOCUMENTS 4,608,183  8/1986  Rossmoore ............................ 252/36

FOREIGN PATENT DOCUMENTS 5-170608   7/1993  Japan ............................ A01N 43/80
5-286815  11/1993  Japan ............................ A01N 43/80

OTHER PUBLICATIONS

Rohm and Haas Company Bulletin CS–584, dated Aug. 1989 entitled "Kathon® MWC Metalworking Fluid Microbicide.".

*Primary Examiner*—Johann Richter
*Assistant Examiner*—Laura R. Cross
*Attorney, Agent, or Firm*—Julie J. L. Cheng

[57] ABSTRACT

The present invention provides a method of stabilizing non-halogenated 3-isothiazolones in aggressive systems with pH above 8.5. The invention also discloses compositions with pH above 8.5, containing non-halogenated 3-isothiazolones and an effective stabilizing amount of a iodine-containing stabilizer.

5 Claims, No Drawings

STABILIZATION OF NON-HALOGENATED 3-ISOTHIAZOLONES IN AGGRESSIVE SYSTEMS

This is a nonprovisional application of prior pending provisional application Ser. No. 60/007,166, filed Nov. 1, 1995.

This invention relates to stabilization of 3-isothiazolones in aggressive systems.

Non-halogenated 3-isothiazolones are known to be used for the preservation of many loci such as wood, paint, adhesive, caulk, mastic, latex, pulp and paper slurries, textile, leather, plastics, cardboard, lubricants, cosmetics, detergents, household products, industrial cooling water, metal working fluid, pigment slurries, photographic processing fluids, and fuels. Some of these loci, particularly metal working fluids, are known to be quite aggressive towards 3-isothiazolones due to high pH. Preservation of metal working fluids such as cutting oils is difficult due to decomposition of the 3-isothiazolones at pH above 8.5. A method of stabilizing non-halogenated 3-isothiazolones in aggressive metal working fluids with pH above 8.5 is desired.

The present invention comprises a method of stabilizing 2-methyl-4-isothiazolin-3-one (MI), 2-n-octyl-4-isothiazolin-3-one (OI), or a mixture thereof in a composition having a pH above 8.5 and which is free of 5-chloro-2-methyl-4-isothiazolin-3-one (CMI), comprising introducing an effective stabilizing amount of an iodine-containing compound selected from the group consisting of iodic acid, periodic acid, and salts thereof.

This invention also relates to compositions having a pH above 8.5 comprising MI, OI, or a mixture thereof and an effective stabilizing amount of an iodine-containing compound selected from the group consisting of iodic acid, periodic acid, salts thereof, said composition being free of chlorinated 3-isothiazolone.

The preferred concentration of the 3-isothiazolone compound(s) in solution is from 750 to 5,000 ppm MI, or from 100 to 2,500 ppm OI, or a mixture thereof, based on the total weight of the system.

The most preferred concentration of the 3-isothiazolone compound(s) in solution is from 2,000 to 2,500 ppm MI, or from 500 to 1,000 ppm OI, or a mixture thereof, based on the total weight of the system.

The preferred concentration of the stabilizer(s) in solution is from 100 to 5,000 ppm, more preferably 1,000 to 3,000 ppm based on the total weight of the system.

Metal salts such as copper sulfate have been disclosed as stabilizers for 3-isothiazolones in metal working fluids. See "Kathon® MWC Bulletin CS-584", page 6, Rohm and Haas Company 1989. Environmental regulations on copper have made the use of copper for stabilizing 3-isothiazolones in metal working fluids unacceptable.

Japanese Tokkyo Koho 05-170608, assigned to Shinto Paint Ltd., disclosed antimicrobial compositions for preventing microbiotic contamination of aqueous dispersions of synthetic high polymers such as synthetic rubber latex, which do not cause coagulation of said dispersions. The compositions contain 3-isothiazolones and a stabilizer or stabilizers selected from bromic acid, iodic acid, periodic acid or their salts. This reference does not teach stabilization of non-halogenated 3-isothiazolones in aggressive metal working fluids with pH above 8.5.

Japanese Kokai Tokkyo Koho 05-286815, assigned to Takeda Pharmaceutical LTD., disclosed industrial germicides containing 3-isothiazolones, alkali metal salt of bromine acid or iodine acid, and water. Potassium bromate was preferred over the other stabilizers. This invention does not teach stabilization of non-halogenated 3-isothiazolones in aggressive metal working fluids with pH above 8.5.

In the following examples, the source of MI was a 50% solution of 2-methyl-4-isothiazolin-3-one in propylene glycol. The source of OI was a 45% solution of 2-n-octyl-4-isothiazolin-3-one in propylene glycol. The source of CMI for Example 1 was a 1.5% solution in water of a 3:1 mixture of CMI:MI. The source of CMI for Example 3 was 99% CMI.

EXAMPLE 1

This example demonstrates that non-chlorinated 3-isothiazolones (MI and OI) are stable in glycol/water solutions, while chlorinated isothiazolone (CMI) is not stable in the same solution. Samples were prepared in 30 ml. screw cap glass vials. Sample 1 was 2.0 g. MI, 4 g. ethylene glycol, and 14.0 g. deionized (DI) water. Sample 2 was 1.46 g. CMI, 9.0 g. ethylene glycol, and 9.54 g. DI water. Sample 3 was 2.20 g. OI, 15.0 g. ethylene glycol, and 2.80 g. DI water. Samples were capped and shaken, then stored at 45° C. for 4 weeks. Analysis was performed by High Pressure Liquid Chromatography (HPLC) with UV detection. Results are shown in Table 1.

TABLE 1

| Sample | AI (%) | % Active Ingredient Remaining | | | | | |
|---|---|---|---|---|---|---|---|
| | | 1 Day | 3 Days | 1 Week | 2 Weeks | 3 Weeks | 4 Weeks |
| 1(MI) | 4.51 | 98.2 | 100 | 98.7 | 99.3 | 104 | 99.3 |
| 2(CMI)* | 4.78 | 96.2 | 90.2 | 85.1 | 76.2 | 69.2 | 63.2 |
| 3(OI) | 5.08 | NA | NA | 100 | 98.0 | 98.2 | 98.4 |

NA = Not Analyzed
* = Comparative

EXAMPLE 2

This comparative example demonstrates the effect of pH on the stability of non-chlorinated 3-isothiazolones in a metal working fluid. Samples were prepared in 30 ml. screw cap glass vials. The low water content of metal working fluid concentrates makes direct pH measurement not relevant, so pH's of 5% aqueous dilutions were measured. To 1 g. metal working fluid was added 19 g. DI water. The pH was measured and the amount of hydrochloric acid (HCl) was measured to adjust the pH of the 5% dilution. A corresponding amount of HCl (20X) was added to the metal working fluid (MWF) itself. The initial pH of the metal working fluid was 9.2. To samples 1, 2, 3, 4, 5, and 6 were added 19.92 g. MWF and 0.08 g. MI. The pH of the MWF was as follows: sample 1=9.2, sample 2=9.0, sample 3=8.5, sample 4=8.1, sample 5=7.6, sample 6=7.0. To samples 7, 8, 9, 10, 11, and 12 were added 19.91 g. MWF and 0.09 g. OI. The pH of the MWF was as follows: sample 7=9.2, sample 8=9.0, sample 9=8.5, sample 10=8.1, sample 11=7.6, sample 12=7.0. Samples were capped and shaken, then stored at room temperature and analyzed by HPLC at 0, 7, 14, 21 and 28 days storage. Results are shown in Table 2.

TABLE 2

Comparative

| Fluid pH | % MI Remaining | | | | % OI Remaining | | | |
|---|---|---|---|---|---|---|---|---|
| | 7 Days | 14 Days | 21 Days | 28 Days | 7 Days | 14 Days | 21 Days | 28 Days |
| 9.2 | 8 | 0 | 0 | 0 | 0 | NA | NA | NA |
| 9 | 64 | 30 | 19 | 16 | 0 | NA | NA | NA |
| 8.5 | 77 | 56 | 43 | 35 | 0 | NA | NA | NA |
| 8.1 | 90 | 76 | 66 | 60 | 74 | 5 | 3 | NA |
| 7.6 | 99 | 90 | 86 | 81 | 100 | 93 | 91 | 92 |
| 7 | 99 | 94 | 95 | 92 | 100 | 100 | 100 | 99 |

EXAMPLE 3

Effect of Stabilizer of Invention

This example demonstrates the effects of the stabilizers of this invention on the stability of CMI, MI, and OI in a metal working fluid. Metal working fluid "A" was used as the fluid for this example. It is a semisynthetic metal working fluid with initial pH of 9.22 (as a 4% aqueous dilution). Samples were prepared in 30 ml. screw cap glass vials. To sample 1 was added 0.04 g. CMI and 19.96 g. MWF "A". To samples 2, 3, 4, 5, and 6 were added 0.04 g. CMI, 0.04 g. stabilizer, and 19.92 g. MWF "A". To sample 2 was added potassium iodate ($KIO_3$), to sample 3 was added sodium periodate ($NaIO_4$), to sample 4 was added sodium bromate ($NaBrO_3$), to sample 5 was added iodic acid ($HIO_3$), and to sample 6 was added periodic acid ($HIO_4$). To sample 7 was added 0.08 g. MI and 19.92 g. MWF "A". To samples 8, 9, 10, 11, and 12 were added 0.08 g. MI, 0.02 g. stabilizer, and 19.90 g. MWF "A". To sample 8 was added $KIO_3$, to sample 9 was added $NaIO_4$, to sample 10 was added $NaBrO_3$, to sample 11 was added $HIO_3$, and to sample 12 was added $HIO_4$. To sample 13 was added 0.09 g. OI and 19.91 g. MWF "A". To sample 14, 15, 16, 17, and 18 was added 0.09 g. OI, 0.04 g. stabilizer and 19.87 g. MWF "A". To sample 14 was added $KIO_3$, to sample 15 was added $NaIO_4$, to sample 16 was added $NaBrO_3$, to sample 17 was added $HIO_3$, and to sample 18 was added $HIO_4$. Samples were capped and shaken, then stored at 40° C. and analyzed by HPLC at 0, 1, 2, 3, and 4 weeks storage. Samples were considered to pass when greater than 50% active ingredient remained after storage. Results are shown in Tables 3 and 4.

TABLE 3

| Stabilizer | Amount (ppm) | % CMI* 1 Week | % OI Remaining | | | |
|---|---|---|---|---|---|---|
| | | | 1 Week | 2 Weeks | 3 Weeks | 4 Weeks |
| None* | 0 | 0 | 0 | NA | NA | NA |
| $KIO_3$ | 2,000 | 0 | 83 | 73 | 57 | 62 |

TABLE 3-continued

| Stabilizer | Amount (ppm) | % CMI* 1 Week | % OI Remaining | | | |
|---|---|---|---|---|---|---|
| | | | 1 Week | 2 Weeks | 3 Weeks | 4 Weeks |
| $NaIO_4$ | 2,000 | 0 | 77 | 76 | 71 | 71 |
| $NaBrO_3$* | 2,000 | 0 | 0 | NA | NA | NA |
| $HIO_3$ | 2,000 | 0 | 89 | 78 | 71 | 75 |
| $HIO_4$ | 2,000 | 0 | 93 | 96 | 84 | 73 |

NA = Not Analyzed

TABLE 4

| Stabilizer | Amount (ppm) | % MI Remaining | | |
|---|---|---|---|---|
| | | 1 Week | 2 Weeks | 3 Weeks |
| None* | 0 | 0 | NA | NA |
| $KIO_3$ | 1,000 | 56 | 2 | NA |
| $NaBrO_3$* | 1,000 | 0 | NA | NA |
| $HIO_3$ | 2,000 | 75 | 74 | 53 |
| $HIO_4$ | 2,000 | 79 | 76 | 70 |

* = Comparative

This example also demonstrates iodic acid, periodic acid, and their salts are effective at stabilizing non-chlorinated 3-isothiazolones in aggressive metal working fluids at pH above 8.5, where bromate salts are ineffective, and that neither iodic acid, periodic acid, their salts, nor bromate is effective to stabilize chlorinated 3-isothiazolones in such fluids.

What is claimed is:

1. Method of stabilizing 2-methyl-4-isothiazolin-3-one, 2-n-octyl-4-isothiazolin-3-one, or a mixture thereof in a composition having a pH above 8.5 and which is free of 5-chloro-2-methyl-4-isothiazolin-3-one, comprising introducing an effective stabilizing amount of an iodine-containing compound selected from the group consisting of iodic acid, periodic acid, salts thereof.

2. Composition having a pH above 8.5 comprising 2-methyl-4-isothiazolin-3-one, 2-n-octyl-4-isothiazolin-3-one, or a mixture thereof and an effective stabilizing amount of an iodine-containing compound selected from the group consisting of iodic acid, periodic acid, salts thereof, said composition being free of 5-chloro-2-methyl-4-isothiazolin-3-one.

3. Composition according to claim 2 in the form of a metal working fluid which comprises a cutting oil.

4. Composition according to claim 2 wherein 2-methyl-4-isothiazolin-3-one is present in a concentration of 750 to 5,000 ppm.

5. Composition according to claim 2 wherein 2-n-octyl-4-isothiazolin-3-one is present in a concentration of 100 to 2,500 ppm.

* * * * *